United States Patent
Miyazawa et al.

[11] Patent Number: 5,900,503
[45] Date of Patent: May 4, 1999

[54] PROCESS FOR PRODUCING OPTICALLY ACTIVE CYANOHYDRINS

[75] Inventors: Yoshinobu Miyazawa, Saitama; Taichi Koshigoe, Higashimatsuyama; Kouichi Ohkawa, Chiba; Jouji Sekine, Yono; Shinichiro Saeki, Tama, all of Japan

[73] Assignee: Nippon Kayaku Kabushiki Kaisha, Tokyo, Japan

[21] Appl. No.: 09/068,605

[22] PCT Filed: Feb. 7, 1997

[86] PCT No.: PCT/JP97/00319

§ 371 Date: May 11, 1998

§ 102(e) Date: May 11, 1998

[87] PCT Pub. No.: WO97/25082

PCT Pub. Date: Aug. 14, 1997

[30] Foreign Application Priority Data

Feb. 8, 1996 [JP] Japan ................................ 8-045647

[51] Int. Cl.$^6$ .................................................. C07C 255/00
[52] U.S. Cl. .......................................................... 558/354
[58] Field of Search ............................................... 558/354

[56] References Cited

U.S. PATENT DOCUMENTS

| | | | |
|---|---|---|---|
| 5,157,143 | 10/1992 | Pellacini et al. | 560/12 |
| 5,493,047 | 2/1996 | Brussee et al. | 558/354 |

FOREIGN PATENT DOCUMENTS

| | | |
|---|---|---|
| 0 211 580 | 2/1987 | European Pat. Off. |
| 2-17165 | 1/1990 | Japan . |
| 2-28144 | 1/1990 | Japan . |
| 1510477 | 5/1978 | United Kingdom . |

OTHER PUBLICATIONS

Tetrahedron Lett. 1988, vol. 29, No. 27; pp. 3295–3298; M. T. Reetz, et al.; "Stereoselective Cyanohydrin–Forming reactions of Chiral α–Amino Aldehydes".

J. Antibiot. 1976, vol. 29, No. 5 pp. 600–601, "The Chemical Synthesis of Bestatin".

Chem. Lett. 1992, No. 7, pp. 1169–1172; Jin–Hua Gu, et al.; "Unique Stereocontrol in Europium (III)–Catalyzed Cyanosilylation of Chiral α–Amino Aldehydes".

Tetrahedron Lett. vol. 33, pp. 5029–5032, 1992; M. Robert Leanna, etal.; "Synthesis of α–Amino and α–Alkoxy Aldehydes via Oxoammonium Oxidation".

Org. Syn., vol. 69, pp. 212–219; Pier Lucio Anelli,et al.; "A General Synthetic Method for the Oxidation of Primary Alcohols to Aldehydes: (S)–(+)–2–Methylbutanal (Butanal, 2–methyl–, (S)–)".

*Primary Examiner*—Deborah Lambkin
*Assistant Examiner*—Joseph Murray
*Attorney, Agent, or Firm*—Nields, Lemack & Dingman

[57] ABSTRACT

An optically active cyanohydrin represented by the following general formula (1):

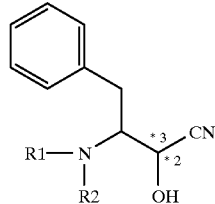

wherein each of R1 and R2 is a hydrogen atom or an amino-protecting group, and the configurations relating to the carbon atoms at the *2-position and *3-position are as follows: in the case of the carbon atom at the *2-position being in R-configuration, the carbon atom at the *3-position is in S-configuration, and in the case of the carbon atom at the *2-position being in S-configuration, the carbon atom at the *3-position is in R-configuration, can be efficiently produced by crystallizing one of the optically active cyanohydrins while treating a mixture of cyanohydrin diastereomers in the presence of an amine and an organic solvent to change the configuration relating to the carbon atom at the 2-position and thereby cause isomerization.

14 Claims, No Drawings

PROCESS FOR PRODUCING OPTICALLY ACTIVE CYANOHYDRINS

TECHNICAL FIELD

The present invention relates to a process for producing an optically active cyanohydrin, more specifically an optically active N-(protected)-3-amino-2-hydroxy-4-phenylbutyronitrile (hereinafter referred to as "optically active AHPBN" in some cases), efficiently in high yield.

The optically active AHPBN according to the present invention is an important compound as an intermediate of bestatin (an anticancer drug), a renin inhibitor (a hypotensive drug), a HIV-treating drug, etc.

BACKGROUND ART

As a process for synthesizing an optically active AHPBN selectively, there is the process described in Tetrahedron Letters, Vol. 29, p. 3295, 1988.

This process, however, is disadvantageous in that the selective synthesis of the optically active AHPBN requires expensive reagents and a reaction condition of a very low temperature of −20° C. or lower. Therefore, this process is not industrially suitable. On the other hand, a process comprising reacting an N-protected-L-phenylalaninal with sodium hydrogensulfite and potassium cyanide (EP-A-211580) can be practiced at ordinary temperature. This process, however, is poor in selectivity for an optically active reaction product, and no method for industrially easy separation of only the optically active reaction product has been known. Therefore, it can give the optically active reaction product only in low yield, and it is unavoidably expensive as a process for obtaining the optically active reaction product.

DISCLOSURE OF THE INVENTION

We earnestly investigated these problems and consequently found the following facts. By treating diastereomers of AHPBN in the presence of an amine and an organic solvent, the configuration relating to the carbon atom at the 2-position can be changed to cause isomerization, and the isomerization can be continued by taking out an optically active substance with a lower solubility, so that the optically active substance with a lower solubility can be obtained in high yield. When an optically active substance such as a (2R, 3S) form of AHPBN is precipitated from one of the following solvents (a) and (b) comprising diastereomers of AHPBN, the desired (2R, 3S) form can be precipitated selectively in high yield: (a) a single ether solvent or a mixed solvent of an ether solvent and aliphatic hydrocarbon solvent, and (b) a mixed solvent of an aromatic hydrocarbon solvent and an aliphatic hydrocarbon solvent. In addition, an optically active AHPBN can be obtained in higher yield by combining the above two methods than by practicing one of them alone. Thus, the present invention has been accomplished.

That is, the present invention relates to the following processes (1) to (14).

(1) A process for producing an optically active cyanohydrin represented by the following general formula (1):

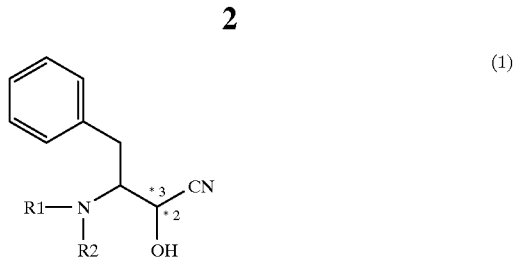

wherein each of R1 and R2 is a hydrogen atom or an amino-protecting group, and the configurations relating to the carbon atoms at the *2-position and *3-position are as follows: in the case of the carbon atom at the *2-position being in R-configuration, the carbon atom at the *3-position is in S-configuration, and in the case of the carbon atom at the *2-position being in S-configuration, the carbon atom at the *3-position is in R-configuration, which comprises treating a mixture of diastereomers of an N-(protected)-3-amino-2-hydroxy-4-phenylbutyronitrile in the presence of an amine and an organic solvent.

(2) A process according to the above process (1), wherein the amount of the amine used is 0.1 to 10 mol % based on the number of moles of the mixture of diastereomers of an N-(protected)-3-amino-2-hydroxy-4-phenylbutyronitrile, and the treatment temperature ranges from 0° C. to reflux temperature.

(3) A process according to the above process (1), wherein the organic solvent is a single ether solvent, a mixed solvent of an ether solvent and an aliphatic hydrocarbon solvent, a single aromatic hydrocarbon solvent, or a mixed solvent of an aromatic hydrocarbon solvent and an aliphatic hydrocarbon solvent.

(4) A process according to the above process (3), wherein each of the mixing ratio of the ether solvent to the aliphatic hydrocarbon solvent and that of the aromatic hydrocarbon solvent to the aliphatic hydrocarbon solvent is 1:0–6.

(5) A process according to the above process (3), wherein the ether solvent is isopropyl ether, the aliphatic hydrocarbon solvent is n-heptane, and the aromatic hydrocarbon solvent is toluene.

(6) A process according to the above processes (1) to (3), wherein the amine is a tertiary amine.

(7) A process according to the above process (6), wherein the amine is triethylamine.

(8) A process according to the above process (1), wherein either R1 or R2 in the general formula (1) is a substituted or unsubstituted benzyloxycarbonyl group, and the other is a hydrogen atom.

(9) A process for producing an optically active cyanohydrin which comprises treating a (2S, 3S)- or (2R, 3R)-N-(protected)-3-amino-2-hydroxy-4-phenylbutyronitrile in the presence of an amine and an organic solvent to obtain a corresponding (2R, 3S) form or (2S, 3R) form, respectively.

(10) A process for producing a (2R, 3S)-N-(protected)-3-amino-2-hydroxy-4-phenylbutyronitrile which comprises treating (2RS, 3S)-N-(protected)-3-amino-2-hydroxy-4-phenylbutyronitrile in the presence of an amine and a mixed solvent of an aromatic hydrocarbon solvent and an aliphatic hydrocarbon solvent in a mixing ratio: 1:2–6.

(11) A process for producing a (2R, 3S)-3-amino-2-hydroxy-4-phenylbutanoic acid which comprises treating (2RS, 3S)-N-(protected)-3-amino-2-hydroxy-4- phenylbutyronitrile in the presence of an amine and an organic solvent to obtain (2R, 3S)-N-(protected)-3-amino-2-hydroxy-4-phenylbutyronitrile, and then hydrolyzing this compound.

(12) A process according to the above process (11), wherein the hydrolysis is carried out at 50° C. to reflux temperature by using 3 to 20 parts by volume of a 10 to 40% aqueous mineral acid solution per part by weight of the (2R, 3S)-N-(protected)-3-amino-2-hydroxy-4-phenylbutyronitrile.

(13) A process for producing a (2R, 3S)-N-protected-3-amino-2-hydroxy-4-phenylbutyronitrile which comprises selectively precipitating the (2R, 3S) form from a solvent comprising diastereomers of N-protected-3-amino-2-hydroxy-4-phenylbutyronitrile, said solvent being (a) a single ether solvent or a mixed solvent of an ether solvent and an aliphatic hydrocarbon solvent, or (b) a mixed solvent of an aromatic hydrocarbon solvent and an aliphatic hydrocarbon solvent.

(14) A process according to the above process (13), which comprises the selective precipitation of the (2R, 3S) form, followed by collecting the precipitated crystals by filtration, and adding an amine to the filtrate to further obtain the (2R, 3S) form from the filtrate.

BEST MODE FOR CARRYING OUT THE INVENTION

The present invention is explained below in further detail.

To obtain an optically active cyanohydrin of the formula (1), i.e., a threo form of (2R, 3S)- or (2S, 3R)-N-(protected)-3-amino-2-hydroxy-4-phenylbutyronitrile in high yield according to the present invention, it is sufficient that a mixture of diastereomers of N-(protected)-3-amino-2-hydroxy-4-phenylbutyronitrile (hereinafter referred to as "cyanohydrin" in some cases) is treated with an amine and an organic solvent. As to a method for the treatment, as explained hereinafter in detail, the diastereomer mixture is brought into contact with, preferably suspended in the amine and the solvent. The optically active cyanohydrin crystals thus precipitated may be collected by a conventional method such as filtration.

As the mixture of cyanohydrin diastereomers used in the present invention, either a (2RS, 3R) form or a (2RS, 3S) form may be used, though the (2RS, 3S) form is preferable. The (2RS, 3R) form and (2RS, 3S) form of the diastereomer mixture may be obtained from D-phenylalaninal and L-phenylalaninal, respectively, by the process described hereinafter. As the mixing proportion of the starting diastereomers corresponding to optically active substances, respectively, any proportion may be employed. As the diastereomer mixture, any mixture may be used so long as it is obtained by a conventional production process of cyanohydrin. The diastereomer mixture may be either wet crystals or dried crystals.

Not only the above-mentioned mixtures but also a pure (2S, 3S) or (2R, 3R) form in some cases may be used. The (2S, 3S) or (2R, 3R) form may also be produced from L-phenylalaninal or D-phenylalaninal, respectively, and extracted as a necessary compound.

An example of process for producing the diastereomer mixture is described below.

A (D or L)-N-(protected)-phenylalaninal is dissolved in a halogenated solvent (e.g. dichloromethane, chloroform, etc.) or an ester solvent (e.g. ethyl acetate, etc.), followed by adding thereto an aqueous sodium hydrogensulfite solution. The resulting solution is cooled and then water and a metal salt of prussic acid, such as sodium cyanide, potassium cyanide or the like are added thereto, whereby a corresponding cyanohydrin is synthesized at room temperature.

After completion of the reaction, the organic layer is separated, washed with water and then concentrated. In this case, the synthesized cyanohydrin is crystallized. If the crystallization is difficult, it is facilitated by seeding with cyanohydrin crystals. The thus crystallized cyanohydrin is isolated by filtration. The cyanohydrin may be used as it is as wet crystals, or it may be used as dried crystals after being dried by a conventional method.

In the above reaction process, each of sodium hydrogensulfite and the metal salt of prussic acid is used usually in an amount of approximately 1.0–1.2 mols per mol of the starting (D or L)-N-(protected)-phenylalaninal.

The starting phenylalaninal is synthesized from phenylalaninol according to the process described in Org. Syn. 69, 212–219 or Tetra. Lett., 33, 5029, 1992.

In the general formula (1), the amino-protecting group for R1 or R2 is not particularly limited and all well-known amino-protecting groups may be used. Preferable examples of the amino-protecting group are acyl type protecting groups (including urethane type protecting groups), for example, (1) lower alkyl (having 1 to 6 carbon atoms)-carbonyl groups which may be substituted by one or more halogen atoms, such as acetyl, trifluoroacetyl, etc., (2) arylcarbonyl groups such as substituted [substituent: nitro, lower alkyl of 1 to 6 carbon atoms, halogen, etc.] or unsubstituted benzoyl, phthalyl, etc., and (3) acyl protecting groups of 1 to 12 carbon atoms, such as substituted [substituent: nitro, lower alkyl of 1 to 6 carbon atoms, halogen, etc.] or unsubstituted benzyloxycarbonyl, alkoxycarbonyl of 1 to 6 carbon atoms, urethane-forming type acyl protecting groups [e.g. cyclo (number of carbon atoms: 5 to 6)-alkanoyloxycarbonyl, etc.], and the like. As other protecting groups, there may be exemplified groups such as benzyl, substituted [substituent: nitro, lower alkyl of 1 to 6 carbon atoms, halogen, etc.] or unsubstituted arylsulfonyl, o-nitrobenzenesulfonyl, trityl, etc. More preferable examples of the amino-protecting groups are urethane type protecting group of 1 to 8 carbon atoms, such as t-butyloxycarbonyl, etc. Particularly preferable examples thereof are substituted [substituent: nitro, lower alkyl of 1 to 6 carbon atoms, halogen, etc.] and unsubstituted benzyloxycarbonyl groups.

Although the treatment carried out in the present invention may be any of immersion, suspension, etc. so long as it brings the starting mixture of cyanohydrin diastereomers into contact with an organic solvent in the presence of an amine, suspension is preferable. Although the treatment time is not particularly limited, it is preferably 30 minutes or more because when it is too short, the purity of the optically active substance is not sufficiently improved. The treatment time is more preferably 1 to 10 hours.

As to the treatment temperature, the treatment is usually carried out at 0° C. to reflux temperature, preferably room temperature to 70° C.

As to the amount of the amine used, the amine is made present in an amount of 0.1 to 10 mol %, preferably 0.5 to 8 mol %, more preferably 1.0 to 5 mol %, based on the number of moles of the mixture of cyanohydrin diastereomers.

Although the kind of the amine used is not particularly limited, mono-, di- or tri-substituted amines having 1 to 3 lower alkyl groups of 1 to 6 carbon atoms as the substituent (s) are preferable. Specific examples of the amine are primary amines such as methylamine, ethylamine, propylamine, butylamine, etc.; secondary amines such as dimethylamine, diethylamine, dipropylamine, diisopropylamine, etc.; and tertiary amines such as trimethylamine, triethylamine, tripropylamine, tributylamine, etc. Tertiary amines substituted by three alkyl groups of 1 to 4 carbon atoms, such as triethylamine, etc. are particularly preferable because they are easy to handle.

As the organic solvent used for the treatment in the present invention, an ether solvent or an aromatic hydrocarbon solvent may be used alone, though a mixed solvent of such a solvent and another solvent is preferable. As the other solvent mixed, an aliphatic hydrocarbon solvent is preferable.

Specific preferable examples of the ether solvent are lower alkyl ($C_1$–$C_4$) ethers such as isopropyl ether, diethyl ether, t-butyl methyl ether, etc. Isopropyl ether is especially preferable.

The aliphatic hydrocarbon solvent includes $C_5$–$C_{10}$ aliphatic hydrocarbon solvents such as n-hexane, n-heptane, n-octane, etc., and n-heptane is especially preferable. The aromatic hydrocarbon solvent includes toluene, xylene, benzene type solvents (unsubstituted benzene or benzene substituted by $C_1$–$C_6$ lower alkyl or halogen), etc., and toluene is preferable.

As the mixed solvent, a mixed solvent of isopropyl ether and n-heptane or a mixed solvent of toluene and n-heptane is especially preferable. The mixed solvent of toluene and n-heptane is the most preferable.

The mixing ratio of the ether solvent to the aliphatic hydrocarbon solvent is usually 1:0–6 by volume, preferably approximately 1:1–2 by volume. The mixing ratio of the aromatic hydrocarbon solvent to the aliphatic hydrocarbon solvent is usually 1:0–6 by volume, preferably 1:2–6 by volume, more preferably approximately 1:4 by volume. The amount of the ether solvent used alone, the mixed solvent thereof used, the aromatic hydrocarbon solvent used alone, or the mixed solvent thereof used is preferably 1 to 10 parts by volume per part by weight of the mixture of cyanohydrin diastereomers.

In the present invention, an optically active cyanohydrin of the formula (1) may be produced without an amine by incorporating the mixture of cyanohydrin diastereomers into the above-mentioned ether solvent, mixed solvent of an ether solvent and an aliphatic hydrocarbon solvent, or mixed solvent of an aromatic hydrocarbon solvent and an aliphatic hydrocarbon solvent, and precipitating the optically active cyanohydrin, for example, a (2R, 3S) form selectively. Such a process may be practiced in the same manner as for the above-mentioned process using an amine and an organic solvent.

In addition, the following is also possible: after the optically active cyanohydrin is obtained by precipitating the same selectively by the former process, an amine is added to a filtrate remaining after the recovery of the optically active cyanohydrin as crystals, and the same process as that described above is practiced, whereby the optically active cyanohydrin is further obtained as crystals from the remaining filtrate.

By the treatment according to the present invention, an optically active substance having a lower solubility in the organic solvent such as an ether solvent may be obtained with a purity higher than that of a corresponding diastereomer in the starting mixture of cyanohydrin diastereomers. For example, when the starting mixture is a (2RS, 3S) form, a (2R, 3S) form having a high purity may be obtained. The (2R, 3S) form having a purity of 90% or more, preferably 97% or more, more preferably 99% or more may be obtained by repeating the treatment according to the present invention as occasion demands.

An optically active threo (2R, 3S)- or (2S, 3R)-3-(protected)-amino-2-hydroxy-4-phenylbutanoic acid may be synthesized by hydrolyzing the optically active cyanohydrin of the formula (1) obtained in the manner described above, i.e., the threo (2R, 3S) form or (2S, 3R) form by, for example, the method disclosed in GB-A-1510477, i.e., a method of hydrolyzing the optically active cyanohydrin at room temperature to reflux temperature, preferably 50° C. to reflux temperature by using 1 to 30 parts by volume, preferably 3 to 20 parts by volume of an aqueous acid solution, preferably an aqueous mineral acid solution (e.g. hydrochloric acid, sulfuric acid, etc.) alone or as a mixed solvent with an organic solvent (e.g. dioxane, tetrahydrofuran, etc.) per part by weight of the optically active cyanohydrin. Usually, the concentration of the aqueous acid solution is approximately 5–50%, preferably 10–40%.

The present invention is concretely explained below with reference to reference examples and examples but is not limited by them.

REFERENCE EXAMPLE 1

Synthesis of benzyloxycarbonyl-phenylalaninal

In 480 ml of methylene chloride were dissolved 45.6 g (160 mmol) of L-benzyloxycarbonyl-phenylalaninol and 10 mg of TEMPO (2,2,6,6-tetramethyl-1-piperidinyloxy, free radical), and a solution of 16.5 g of sodium bromide in 80 ml of water was added thereto. To water were added 39.2 g of sodium hydrogencarbonate and 100.64 g of a 12% aqueous sodium hypochlorite solution to effect dissolution, and the resulting solution was added dropwise to the above-mentioned aqueous solution at 0–10° C. After the reaction was carried out at 0–10° C. for 1 hour, the reaction solution was allowed to stand and the organic layer was separated, washed with 208 ml of a solution of 1.33 g of potassium iodide in a 10% potassium hydrogensulfate solution, 107 ml of a 10% sodium thiosulfate solution and 100 ml of water, and then concentrated. The concentrate may be used in a subsequent reaction, or crystals may be obtained by crystallizing benzyloxycarbonyl-phenylalaninal by adding 500 ml of n-hexane to the concentrate.

Dried crystals: 44.66 g. Yield: 92%. $^1$H NMR (CDCl$_3$) δ 3.15 (d, 2H), 4.52 (q, 1H), 5.12 (s, 2H), 5.24 (d, 1H), 7.12–7.35 (m, 10H), 9.65 (S, 1H).

REFERENCE EXAMPLE 2

Synthesis of a mixture of cyanohydrin diastereomers

In 520 ml of ethyl acetate was dissolved 41.71 g (147.2 mmol) of L-benzyloxycarbonyl-phenylalaninal. A solution of 19.96 g of sodium hydrogensulfite in 160 ml of water was added thereto. The resulting solution was cooled to 0–10° C., followed by adding dropwise thereto a solution of 9.08 g of sodium cyanide in 160 ml of water. After the dropwise addition, the resulting mixture was allowed to warm to room temperature and subjected to reaction for 6 to 8 hours. After completion of the reaction, the organic layer was separated and then washed with 150 ml of a saturated aqueous sodium chloride solution, and dehydrated with sodium sulfate. The sodium sulfate was filtered off and the filtrate was concentrated. The concentrate may be used as it is in a subsequent reaction. By adding 300 ml of isopropyl ether and 100 ml of n-heptane to the concentrate, a cyanohydrin was crystallized. The crystals were collected by filtration and dried under reduced pressure at room temperature.

Dried crystals: 41.35 g. Yield from phenylalaninal: 90.5%.

As a result of HPLC analysis, the obtained crystals were found to be a mixture of (2R, 3S) form (threo) and (2S, 3S) form (erythro) in a ratio of 65:35.

$[\alpha]^{20}{}_D$=−69.9° (C=1, CH$_3$OH).

REFERENCE EXAMPLE 3

Synthesis of a mixture of cyanohydrin diastereomers

To a solution of 28.3 g of N-benzyloxycarbonyl-L-phenylalaninal in 100 ml of ethyl acetate was added a solution of 11.4 g of sodium pyrosulfite in 100 ml of water at room temperature, and stirred for 1 hour. Then, a solution of 4.9 g of sodium cyanide in 40 ml of water was added dropwise thereto, and the reaction was carried out at room temperature for 2 hours. After completion of the reaction, the organic layer was separated, washed with 60 ml of a saturated aqueous sodium chloride solution, and then dried with anhydrous sodium sulfate. The sodium sulfate was filtered off and the filtrate was concentrated under reduced pressure to obtain a mixture of diastereomers of 3-benzyloxycarbonylamino-2-hydroxy-4-phenylbutyronitrile as concentration residue. As a result of HPLC analysis, the obtained mixture was found to be a mixture of (2R, 3S) form (threo) and (2S, 3S) form (erythro) in a ratio of 64:36.

EXAMPLE 1

Synthesis of a (2R, 3S)-optically active cyanohydrin i) To 37.2 g of the threo-erythro mixture (threo:erythro=65:35) obtained in Reference Example 2 was added 335 g of isopropyl ether, and the resulting suspension was kept at 45° C. for 5 hours. The suspension was cooled to room temperature and the crystals precipitated were collected by filtration and washed with isopropyl ether. The crystals were dried under reduced pressure at room temperature.

Dried crystals: 22.44 g (yield: 55.0%).

As a result of HPLC analysis, the obtained crystals were found to be a mixture of threo form and erythro form in a ratio of 98:2.

$[\alpha]^{20}{}_D$=−80.5° (C=1, CH$_3$OH).

ii) When 0.09 g of triethylamine was added to the filtrate and the resulting mixture was stirred at 50° C. for 10 hours, crystals were slowly precipitated. After the mixture was cooled to room temperature, the crystals were collected by filtration and washed with isopropyl ether. The crystals were dried under reduced pressure at room temperature.

Dried crystals: 7.85 g (total yield from i) and ii): 76.0%).

As a result of HPLC analysis, the obtained crystals were found to be a mixture of threo form and erythro form in a ratio of 93:7.

$[\alpha]^{20}{}_D$=−79.8° (C=1, CH$_3$OH).

EXAMPLE 2

Synthesis of a (2R, 3S)-optically active cyanohydrin

To 13.0 g of the threo-erythro mixture (threo:erythro=65:35) obtained in Reference Example 2 were added 39 g of isopropyl ether and 0.11 g of triethylamine, and the resulting suspension was kept at 50° C. for 5 hours. The suspension was cooled to room temperature and the crystals precipitated were collected by filtration and washed with isopropyl ether. The crystals were dried under reduced pressure at room temperature.

Dried crystals: 10.58 g (yield: 76.8%).

As a result of HPLC analysis, the obtained crystals were found to be a mixture of threo form and erythro form in a ratio of 98:2.

$[\alpha]^{20}{}_D$=−80.6° (C=1, CH$_3$OH).

EXAMPLE 3

Synthesis of a (2R, 3S)-optically active cyanohydrin

To 5.0 g of the threo-erythro mixture (threo:erythro=65:35) obtained in Reference Example 2 were added 15 g of isopropyl ether, 15 g of n-heptane and 0.04 g of triethylamine, the resulting suspension was stirred at 50° C. for 43 hours. The suspension was cooled to room temperature and the crystals precipitated were collected by filtration and washed with isopropyl ether. The crystals were dried under reduced pressure at room temperature.

Dried crystals: 4.34 g (yield: 86.8%).

As a result of HPLC analysis, the obtained crystals were found to be a mixture of threo form and erythro form in a ratio of 99:1.

$[\alpha]^{20}{}_D$=−81.0° (C=1, CH$_3$OH). 200 MHz $^1$H NMR (CDCl$_3$) δ 3.01 (m, 2H), 4.04 (b, 1H), 4.49 (b, 1H), 4.56 (b, 1H), 5.06 (s, 2H), 5.30 (d, 1H), 7.16–7.35 (m, 10H).

EXAMPLE 4

Synthesis of a (2R, 3S)-optically active cyanohydrin

To the diastereomer mixture (threo:erythro=64:36) obtained in Reference Example 3 were added 40 ml of toluene and then 160 ml of n-heptane, and stirred. Then, 0.5 g of triethylamine was added thereto and the resulting mixture was heated with stirring at 45–50° C. for 2 hours. The crystals precipitated were collected by filtration, washed with n-heptane, and then dried to obtain 27.9 g (yield: 90%) of the desired compound (2R, 3S)-3-benzyloxycarbonylamino-2-hydroxy-4-phenylbutyronitrile as white crystals. As a result of HPLC analysis, the obtained crystals were found to be a mixture of threo form and erythro form in a ratio of 95:5.

M.p. 109–110° C.

$[\alpha]^{20}{}_D$=−80.2° (C=1, CH$_3$OH). $^1$H NMR (CDCl$_3$) δ (ppm) 3.01 (m, 2H), 4.04 (b, 1H), 4.49 (b, 1H), 4.56 (b, 1H), 5.06 (s, 2H), 5.30 (d, 1H), 7.16–7.35 (m, 10H).

As shown above, the analysis results agreed with the data obtained in Example 3.

EXAMPLE 5

Synthesis of (2R, 3S)-3-amino-2-hydroxy-4-phenylbutanoic acid

To 10.0 g of a (2R, 3S)-optically active cyanohydrin (threo:erythro=99:1) obtained by the same procedure as in Example 3 were added 85 ml of dioxane and 85 ml of 35% hydrochloric acid, followed by heat treatment at 80° C. for 7 hours. After completion of the reaction, the reaction mixture was cooled to room temperature and 100 ml of isopropyl ether was added thereto and stirred. Subsequently, the aqueous layer was separated and then concentrated to dryness, followed by adding thereto 55 ml of water, and the resulting mixture was adjusted to pH 6 with 28% aqueous ammonia. After the mixture was stirred at room temperature for 6 hours, the crystals precipitated were collected by filtration and washed with water. The crystals were dried under reduced pressure at 50° C.

Dried crystals: 6.01 g (yield: 95.54%).

As a result of HPLC analysis, the obtained crystals were found to be a mixture of threo form and erythro form in a ratio of 99.7:0.3.

$[\alpha]^{20}_D = -31.7°$ (C=1, AcOH).

INDUSTRIAL APPLICABILITY

The present invention makes it possible to produce an optically active cyanohydrin efficiently in high yield. The optically active cyanohydrin obtained according to the present invention is an important compound as an intermediate for synthesis of bestatin (an anticancer drug), a renin inhibitor (a hypotensive drug), a HIV-treating drug, etc.

We claim:

1. A process for producing an optically active cyanohydrin represented by the following general formula (1):

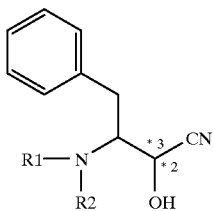

wherein each of R1 and R2 is a hydrogen atom or an amino-protecting group, and the configurations relating to the carbon atoms at the *2-position and *3-position are as follows: in the case of the carbon atom at the *2-position being in R-configuration, the carbon atom at the *3-position is in S-configuration, and in the case of the carbon atom at the *2-position being in S-configuration, the carbon atom at the *3-position is in R-configuration, which comprises treating a mixture of diastereomers of an N-(protected)-3-amino-2-hydroxy-4-phenylbutyronitrile in the presence of an amine and an organic solvent.

2. A process according to claim 1, wherein the amount of the amine used is 0.1 to 10 mol % based on the number of moles of the mixture of diastereomers of an N-(protected)-3-amino-2-hydroxy-4-phenylbutyronitrile, and the treatment temperature ranges from 0° C. to reflux temperature.

3. A process according to claim 1, wherein the organic solvent is a single ether solvent, a mixed solvent of an ether solvent and an aliphatic hydrocarbon solvent, a single aromatic hydrocarbon solvent, or a mixed solvent of an aromatic hydrocarbon solvent and an aliphatic hydrocarbon solvent.

4. A process according to claim 3, wherein each of the mixing ratio of the ether solvent to the aliphatic hydrocarbon solvent and that of the aromatic hydrocarbon solvent to the aliphatic hydrocarbon solvent is 1:0–6.

5. A process according to claim 3, wherein the ether solvent is isopropyl ether, the aliphatic hydrocarbon solvent is n-heptane, and the aromatic hydrocarbon solvent is toluene.

6. A process according to any one of claims 1 to 3, wherein the amine is a tertiary amine.

7. A process according to claim 6, wherein the amine is triethylamine.

8. A process according to claim 1, wherein either R1 or R2 in the general formula (1) is a substituted or unsubstituted benzyloxycarbonyl group, and the other is a hydrogen atom.

9. A process for producing an optically active cyanohydrin which comprises treating a (2S, 3S)- or (2R, 3R)-N-(protected)-3-amino-2-hydroxy-4-phenylbutyronitrile in the presence of an amine and an organic solvent to obtain a corresponding (2R, 3S) form or (2S, 3R) form, respectively.

10. A process for producing a (2R, 3S)-N-(protected)-3-amino-2-hydroxy-4-phenylbutyronitrile which comprises treating (2RS, 3S)-N-(protected)-3-amino-2-hydroxy-4-phenylbutyronitrile in the presence of an amine and a mixed solvent of an aromatic hydrocarbon solvent and an aliphatic hydrocarbon solvent in a mixing ratio: 1:2–6.

11. A process for producing a (2R, 3S)-3-amino-2-hydroxy-4-phenylbutanoic acid which comprises treating (2RS, 3S)-N-(protected)-3-amino-2-hydroxy-4-phenylbutyronitrile in the presence of an amine and an organic solvent to obtain (2R, 3S)-N-(protected)-3-amino-2-hydroxy-4-phenylbutyronitrile, and then hydrolyzing this compound.

12. A process according to claim 11, wherein the hydrolysis is carried out at 50° C. to reflux temperature by using 3 to 20 parts by volume of a 10 to 40% aqueous mineral acid solution per part by weight of the (2R, 3S)-N-(protected)-3-amino-2-hydroxy-4-phenylbutyronitrile.

13. A process for producing a (2R, 3S)-N-protected-3-amino-2-hydroxy-4-phenylbutyronitrile which comprises selectively precipitating the (2R, 3S) form from a solvent comprising diastereomers of N-protected-3-amino-2-hydroxy-4-phenylbutyronitrile, said solvent being (a) a single ether solvent or a mixed solvent of an ether solvent and an aliphatic hydrocarbon solvent, or (b) a mixed solvent of an aromatic hydrocarbon solvent and an aliphatic hydrocarbon solvent.

14. A process according to claim 13, which comprises the selective precipitation of the (2R, 3S) form, followed by collecting the precipitated crystals by filtration, and adding an amine to the filtrate to further obtain the (2R, 3S) form from the filtrate.

* * * * *